(12) United States Patent
Kopaciewicz et al.

(10) Patent No.: US 6,869,572 B1
(45) Date of Patent: Mar. 22, 2005

(54) HIGH DENSITY CAST-IN-PLACE SAMPLE PREPARATION CARD

(75) Inventors: William Kopaciewicz, West Newbury, MA (US); Cheryl Brucato, Andover, MA (US)

(73) Assignee: Millipore Corporation, Bedford, MA (US)

( * ) Notice: Subject to any disclaimer, the term of this patent is extended or adjusted under 35 U.S.C. 154(b) by 85 days.

(21) Appl. No.: 09/659,241

(22) Filed: Sep. 11, 2000

Related U.S. Application Data

(60) Provisional application No. 60/195,780, filed on Apr. 10, 2000, and provisional application No. 60/153,606, filed on Sep. 13, 1999.

(51) Int. Cl.[7] .............................................. B01D 29/05
(52) U.S. Cl. .................... 422/101; 210/323.1; 210/348; 210/406; 210/483; 422/69; 435/288.4; 435/297.5; 435/305.2
(58) Field of Search ................... 422/69, 101; 210/348, 210/406, 483, 323.1; 435/288.4, 297.5, 305.2

(56) References Cited

U.S. PATENT DOCUMENTS

| | | | | |
|---|---|---|---|---|
| 3,759,393 A | * | 9/1973 | Tate et al. .................. | 210/491 |
| 3,888,770 A | | 6/1975 | Avital et al. ................ | 210/238 |
| 4,504,392 A | * | 3/1985 | Groteke ...................... | 210/471 |
| 4,734,192 A | | 3/1988 | Champion et al. .......... | 210/335 |
| 4,797,259 A | * | 1/1989 | Matkovich et al. ......... | 422/101 |
| 4,948,564 A | | 8/1990 | Root et al. .................. | 422/101 |
| 5,009,780 A | | 4/1991 | Sarrasin ...................... | 210/238 |
| 5,108,704 A | * | 4/1992 | Bowers et al. | |
| 5,141,719 A | * | 8/1992 | Fernwood et al. | |
| 5,260,571 A | | 11/1993 | Cottrell et al. .............. | 250/288 |
| 5,401,466 A | | 3/1995 | Foltz et al. .................. | 422/56 |
| 5,605,798 A | | 2/1997 | Koster ......................... | 435/6 |
| 5,705,813 A | | 1/1998 | Apffel et al. ................ | 250/288 |
| 5,719,060 A | | 2/1998 | Hutchens et al. ........... | 436/174 |
| 5,939,024 A | * | 8/1999 | Robertson ................... | 422/101 |
| 5,955,729 A | | 9/1999 | Nelson et al. ............... | 250/282 |
| 6,004,770 A | | 12/1999 | Nelson ........................ | 435/23 |
| 6,020,208 A | | 2/2000 | Hutchens et al. ........... | 436/174 |
| 6,027,942 A | | 2/2000 | Hutchens et al. ........... | 436/173 |
| 6,159,368 A | * | 12/2000 | Moring et al. .......... | 210/321.75 |
| 6,164,457 A | * | 12/2000 | Schlor ......................... | 210/455 |

FOREIGN PATENT DOCUMENTS

WO    WO 98/37949    * 9/1998

* cited by examiner

Primary Examiner—Jan M. Ludlow
(74) Attorney, Agent, or Firm—Nields & Lemack

(57) ABSTRACT

A card or insert having a plurality of recesses for a sample preparation device, the card containing cast-in-place composite and/or non-filled structures which are useful as sorptive or reactive media or for size-based separations. Any particular card size or configuration can be used, and the inclusion of a large amount of adsorptive particles in polymer is achieved while still maintaining the membrane three dimensional structure. In a first preferred embodiment, the composite structures comprise particles entrapped within a porous polymeric substrate, and are cast in-place into a plurality of recesses in an insert for a multi-well sample preparation device, thereby providing an effective platform for high throughput micromass handling. With the appropriate selection of particle chemistry, virtually any separation or purification operation can be conducted in multiplicity, including selective bind/elute chromatography operations, on sample mass loads less than 1 microgram in volumes of a few microliters, as well as larger mass loads and volumes. Manufacturing flexibility and high throughput is achieved. The card can be configured for direct analysis of bound sample without elution.

22 Claims, 12 Drawing Sheets

US 6,869,572 B1

HIGH DENSITY CAST-IN-PLACE SAMPLE PREPARATION CARD

This appln claims benefit to Provisional applications 60/153,606 Sep. 13, 1999 and 60/195,780 Apr. 10, 2000.

BACKGROUND OF THE INVENTION

Test plates for chemical or biochemical analysis which contain a plurality of individual wells or reaction chambers are well known laboratory tools. Such devices have been employed for a broad variety of purposes and assays, and are exemplified in U.S. Pat. Nos. 4,734,192 and 5,009,780, for example. Microporous membrane filters and filtration devices containing the same have become especially useful with many of the recently developed cell culture techniques, assays, and sample preparation methods, especially in the fields of virology, immunlogy, genetics, drug discovery, etc. Typically, a 96-well filtration plate is used to conduct multiple sample preparations or assays simultaneously. One such filtration device commercially available from Millipore Corporation under the name "Multiscreen" is a 96-well filter plate that can be loaded with adsorptive filter materials or particles. However, with the thousands of samples that can be analyzed in a single day for genotyping, for example, even a 96-well plate, which allows the simultaneous treatment of 96 samples, can be inadequate.

In addition, flexibility in the dimensions of multi-well plates is desirable in view of the wide variety of applications that can be performed. Membrane type, well geometry and layout are important criteria in choosing the appropriate sample preparation device for a particular operation. Furthermore, many modern analytical techniques such as matrix assisted laser desorption ionization, time of flight, mass spectrometry (MALDI TOF MS) and 96× capillary electrophoresis systems require only a small amount of sample for analysis. Traditional 96-well devices often contain far more volume than is required for these high performance analytical instruments.

It would therefore be desirable to provide a multi-well plate that allows for the simultaneous treatment of hundreds or thousands of samples. It also would be desirable to provide a multi-well sample preparation array that is easily manufacturable and reproducible, thereby providing flexibility in design to accommodate a particular application.

It also would be desirable to produce a sample preparation array that can process smaller sample volumes.

It also would be desirable to produce a sample preparation array suitable for direct analysis by MALDI TOF mass spectrometry.

SUMMARY OF THE INVENTION

The problems of the prior art have been overcome by the present invention, which provides a card or insert for a single or multi-well sample preparation device, and provides the mechanical apparatus containing and optionally operating the card or insert. The device is a housing that is configured to receive one or more of the inserts. Preferably the inserts are readily removable from the housing, allowing interchangeability with other inserts having the same or different sample preparation characteristics from the previous insert. The housing contains or is in fluid communication with a sample reservoir and a collection reservoir, and a suitable driving force such as pressure, vacuum, centrifugation, or simply capillary action may be used to effectuate the fluid movement. The inserts contain the separations media, the properties and geometry of which may be tailored to the specific action to be carried out. High throughput sample preparation devices that can be applied to a variety of biochemical and chemical applications, for example, are thus provided.

Also disclosed is a method for casting-in-place composite (filled) and/or non-filled structures which are useful as sorptive or reactive media or for size-based separations into one or more apertures in the inserts. In one embodiment, the structures are monolithic and/or continuous. The invention is applicable to a variety of particular sizes and configurations, and provides a means of affixing chromatographic media in a variety of volumes and layouts. The invention enables the inclusion of a substantial (relative to the increase in surface area of the precipitated polymeric structure) amount of media in the polymer composite matrix.

In one embodiment, the composite structures comprise particles entrapped within a porous polymeric substrate, and are cast in-place into a planar or substantially planar insert having one or more recesses, thereby providing an effective platform for high throughput micromass handling. With the appropriate selection of particle chemistry, virtually any separation or purification operation can be conducted in multiplicity, including selective bind/elute chromatography operations, on sample mass loads less than 1 microgram in volumes of a few microliters or less, as well as larger mass loads and volumes. These structures preferably are self-retaining and/or self-supporting.

In addition, the present invention provides for direct analysis, such as by MPLI time-of-flight (TOF) mass spectrometry, of samples without elution. This is accomplished by configuring the insert such that it is compatible with conventional mass spectrometers and can be appropriately positioned in the spectrometer for direct analysis.

In another embodiment, unfilled structures which are preferably self-retaining and/or self-supporting are cast in situ into one or more wells in a suitable insert and can be in used for either size-based or adsorptive separations wherein the cast structure acts as a semi-permeable barrier, or for adsorption. The adsorptive properties of a non-particle filled structure can be imparted either through the native properties of the polymer(s) used or by subsequent derivatization.

In another embodiment, either the filled or unfilled structures which may be self-retaining and/or self-supporting are derived from inorganic materials such as metals or ceramics.

BRIEF DESCRIPTION OF THE DRAWINGS

This application has at least one drawings executed in color. Copies of this patent or patent application with color drawing(s) will be provided by the office upon request and payment of the necessary fee.

DETAILED DESCRIPTION OF THE INVENTION

Figure 1A:
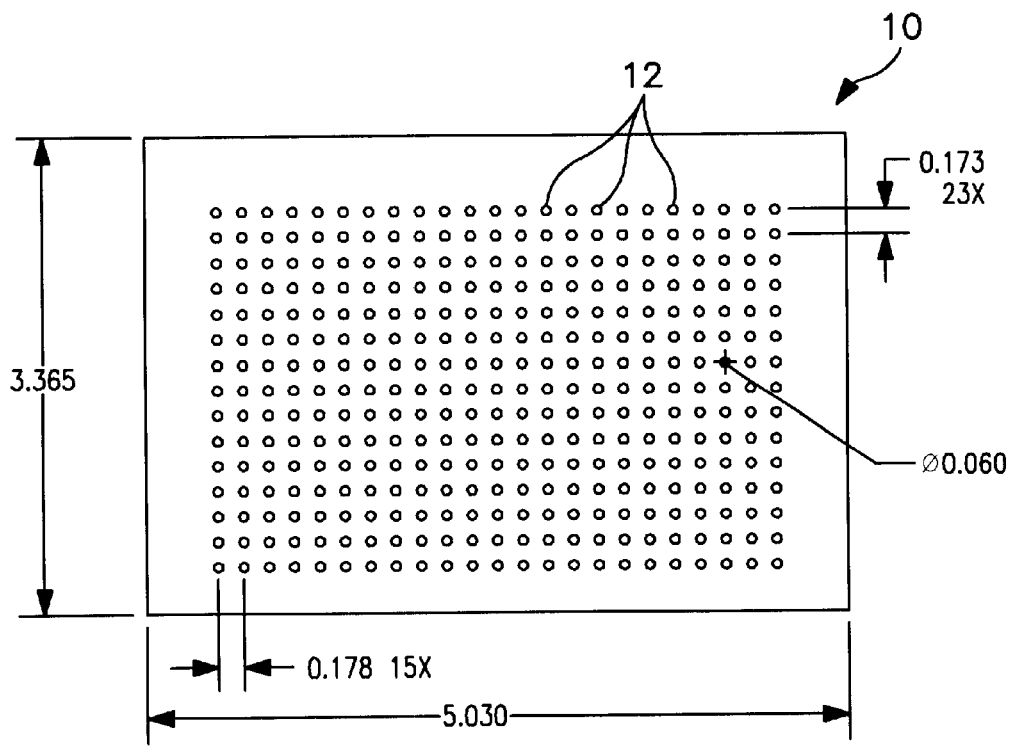
FIGS. 1A and 1B are top views of multi-well filtration cards in accordance with the present invention.

The term "membrane" as used herein includes permeable and semi-permeable three dimensional structures with or without particles, having a porosity suitable for the desired application. The term "composite structure" as used herein includes filled membranes.

Those skilled in the art will recognize that many different particles can be used in the composite structures, depending upon the desired objectives of the resulting device. In the case of adsorptive devices, the ideal device will have rapid adsorption kinetics, a capacity and selectivity commensurate with the application, and allows for elution of bound analyte with an appropriate desorption agent. Suitable adsorptive composite structures are polymer bound, particle laden adsorptive membrane structures, such as those comprised of chromatographic beads which have been adhered together with a binder. A suitable particle loaded structure is comprised of about 80% w/w C18 silica and 20% w/w polysulfone binder, and is produced by Millipore Corporation. Functional composite structures comprising other micronsize (e.g., 1–30 microns) resin particles derivatized with other functional groups are also beneficial, including styrenedivinyl-benzene-based media (unmodified or derivatized with e.g., sulphonic acids, quaternary amines, etc.); silica-based media (unmodified or derivatized with $C_2$, $C_4$, $C_6$, $C_8$, or $C_{18}$, or ion exchange functionalities) to accommodate a variety of applications for peptides, proteins, nucleic acids, and other organic compounds. Those skilled in the art will recognize that other matrices with alternative selectivities (e.g., hydrophobic interaction, affinity, etc.) also can be used, depending on the class of molecules to be separated. The term "particles" as used herein is intended to encompass particles having regular (e.g., spherical) or irregular shapes, as well as shards, fibers and powders, including metal powders, plastic powders (e.g., powdered polystyrene), silica and activated carbon. For example, the addition of silica into a polysulfone polymer results in increased active surface area and is suitable for various applications. Polysulfone sold under the name UDEL P3500 and P1700 by Amoco is particularly preferred in view of the extent of the adherence of the resulting composite structure to the housing (e.g., the walls of the apertures of the inserts), including polypropylene, polyethylene, polystyrene, polycarbonate, etc., and mixtures thereof. Other suitable polymer binders include polyethersulfone, cellulose acetate, cellulose acetate butyrate, acrylonitrile PVC copolymer (sold commercially under the name "DYNEL"), polyvinylidene fluoride (PVDF, sold commercially under the name "KYNAR"), polystyrene and polystyrene/acrylonitrile copolymer, etc. Any castable, membrane-forming polymer (such as nylon) can be used in the invention although viscosity may need to be adjusted and/or the use of mechanical supports may be needed to keep the material in place until precipitated. Adhesion to the housing (e.g., the surface of the walls of the apertures in the inserts) can be enhanced or an analogous effect achieved with these composite structures by means known to those skilled in the art, including etching of the housing, such as with plasma treatment or chemical oxidation; mechanical aids such as rims inside the housing; and inclusion of additives into the housing material that promote such adhesion. Adhesion allows uniform precipitation during casting.

In the preferred method, the formed structures are cast in situ in the recesses or wells of the desired insert using a phase inversion process. This results in the ability to include large amounts of media in the polymer matrix while still maintaining a three-dimensional porous structure. Preferably the membranes or composite structures formed as defined by the well geometry have an aspect ratio (average diameter to average thickness) of less than about 20, more preferably less than about 10, especially less than 2, most preferably from about 0.5 to about 2. For bind/elute applications, an aspect ratio within these ranges provides for suitable residence times of the sample in the composite structure during operation.

In the polymer phase inversion process, the solvent for the polymer must be miscible with the quench or inversion phase. For example, N-methyl-pyrolidone is a suitable solvent for polysulfones, polyethersulfones and polystyrene. In the latter case, polystyrene pellets can be dissolved in N-methyl-pyrolidone and cast-in-place. The resulting structure shows good adhesion to the walls of the wells in the insert, particularly when the insert is plastic, and has adsorption characteristics similar to polysulfone. Dimethylsulfoxide (DMSO), dimethylformamide, butyrolactone, and sulfalane are also suitable solvents. N,N-dimethylacetamide (DMAC) is a suitable solvent for PVDF. Water is the preferred precipitant. Although the water can have a wide temperature range to be effective as a precipitant, higher temperatures (about 80° C.) tend to improve structure permeability. In the evaporative casting process, a volatile solvent for the polymer binder is used. For example, in the case of cellulose acetate, acetone is a suitable volatile solvent. Evaporative casting generally results in a structure which shrinks upon setting. With this method, particles in the filled structures should be at least about 30μ to allow flow through the interstitial spaces after shrinkage without having to apply higher driving force.

When particles are used, the upper limit of particle amounts is dictated by casting solution viscosity. Depending on particle type, up to 40% (w/w) of particles can be added to the polymer solution without resulting in a casting lacquer too viscous for dispensing into the housing. Higher particle loadings may be achieved using higher temperature to reduce viscosity. Suitable particle sizes include particles in the range of from about 100 nanometers to about 100 microns in average diameter with or without porosity.

Any suitable means can be used to deliver lacquer into the wells or apertures of the insert. This can occur simply due to gravity, but also can be assisted using a driving force such as pressure, or can be accomplished by directing the lacquer into the wells using a flat edge such as a knife or spatula blade. The lacquer also could be precisely dispensed into each well. In one embodiment, a sufficient amount of lacquer is simply poured onto the insert and excess removed with a straight edge.

Turning now to FIG. 1, there is shown one embodiment of the insert 10 in accordance with the present invention. The material of construction for the housing, such as a card or an insert, is not particularly limited, but should be made of a material which will not deleteriously react with the reagents used during the sample preparation procedure or any subsequent procedure. The material also must withstand the conditions typical of the method, particularly where pressure is used as the fluid driving force. Suitable materials include plastics (such as polyolefins, especially polyethylene and polypropylene; PVC and polystyrene), glass and stainless steel. Polyolefins, and particularly polypropylene, are preferred insert materials in view of the chemical adhesion that is created with the composite structure when the composite containing polysulfone, and in particular UDEL P3500 and P1700 polysulfones available from Amoco, or polystyrene, in particular, STYRON 685D available from The Dow Chemical Company, is cast-in-place therein. When chemical adhesion of the composite structure to the aperture walls is desired but is insignificant or non-existent, mechanical means can be used to maintain the composite structure in the aperture. such as crimping, press fitting, heat shrinking the housing or a portion thereof, plasma treating the housing or a portion thereof, or chemically treating, such as etching, the housing or a portion thereof to promote adhesion. An advantage of adhesion to the aperture walls is the ability to "seal" the composite structure to the walls without mechanical means. Such sealing (by whatever method) prevents the sample from channeling or bypassing the composite during operation.

Figure 1B:
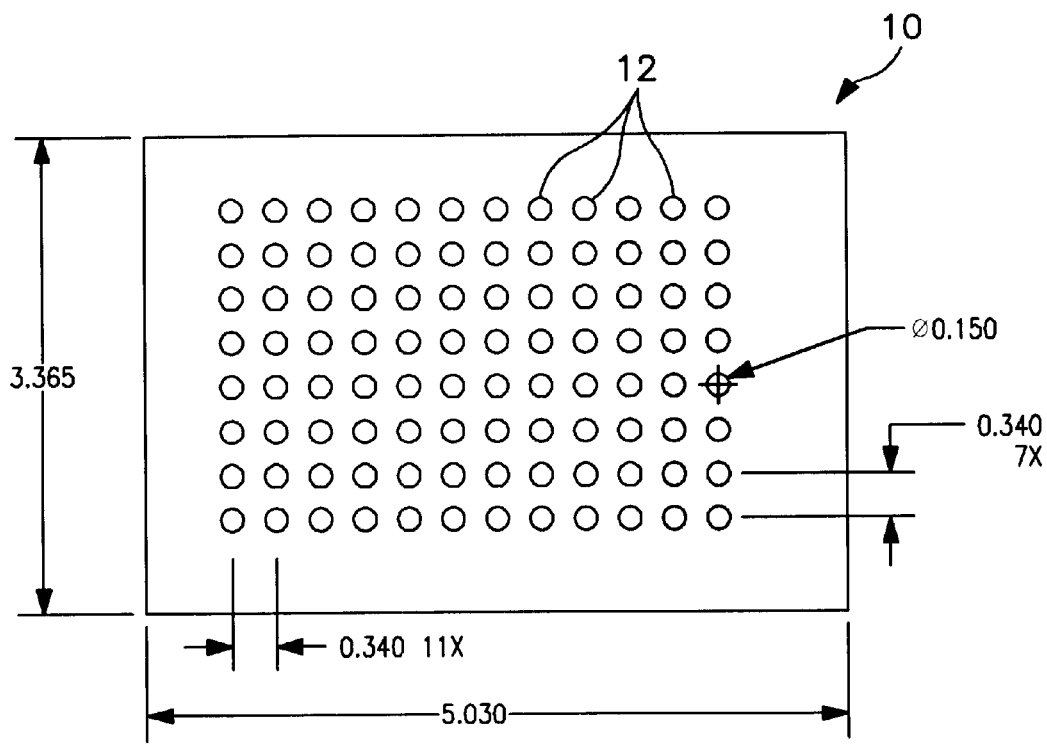

The particular dimensions of the housing 10 and number of recesses or apertures therein are not critical. Where a plurality of apertures are present, the housing forms a high-density sample array. By way of illustration, the housing shown is a 3.365"×5.030" planar card or plate, containing 384 recesses or apertures 12, and is 0.090 inches thick. The apertures 12 penetrate through the housing. Smaller or larger housings can be used, as can thicker or thinner housings. Preferably the housing is planar or substantially planar. The apertures 12 can be formed in the housing by any suitable means, such as drilling, punching or molding. Preferably the apertures 12 are evenly spaced. For example, in the 384 well plate embodiment mentioned above, the apertures 12 have a diameter of about 0.060 inches and are spaced at about 0.178" centers. FIG. 1B shows another embodiment with 96 apertures 12, each with a diameter of 0.150 inches and spaced 0.354 inch centers. The card of FIG. 1B is 0.09 inches thick.

The preferred configuration of the recesses or apertures 12 is substantially cylindrical, as the flow vectors during operation are substantially straight, similar to chromatography, thereby minimizing or avoiding dilutional washing that might occur with non-cylindrical configurations. However, other configurations can be used and are within the scope of the present invention. Preferably the recesses have an open top and an open bottom opposing and spaced from the open top, and thus are coplanar with the top and bottom surfaces of the housing. The composite structure contained in the recesses preferably fills each recess, but can occupy less than the total volume of each recess if desired. Thus, the composite structure is preferably coterminous with both sides of the recess, but can fill less than the entire recess so as to form a distribution well for the introduction of liquid sample, for example.

Preferably the structures of the present invention have a final bed height of from about 0.005 to about 0.5 inches. The ideal bed heights will depend upon the application and are readily determined by those skilled in the art. Bed height is predominantly controlled by the housing thickness; the structures are preferably coterminous with the two sides of the housing that communicate with the recess or recesses. In the embodiment where the housing is planar such as a plate, the structures are preferably coplanar with the two sides of the housing that communicate with the recess or recesses.

The composite structures and the multi-well filtration devices of the present invention containing the composite structures have a wide variety of applications, depending upon the particle selection. For example, applications include peptide and protein sample preparation prior to analysis, peptide removal from carbohydrate samples, amino acid clean-up prior to analysis, immobilized enzymes for micro-volume reactions, immobilized ligands for microaffinity chromatography, isolation of supercoiled and cut plasmids, clean-up of PCR and DNA products, immobilized oligo dT for RNA isolation, dye terminator removal, sample preparation for elemental analysis, etc. Those skilled in the art will be able to choose the appropriate particles, polymer binder, particle chemistry and recess geometry depending upon the desired application. In some cases, a mixture of particles can be used in the same devices. Alternatively or in addition, different chemistries for separate wells can be used.

In the embodiment where the structures of the present invention are not filled with particles, symmetrical or asymmetrical semi-permeable structures, or a combination of symmetrical and asymmetrical semi-permeable polymeric structures, can be formed. In this embodiment, the preferred method of formation is casting in situ in the wells of the insert to form a self-retaining, self-supporting structure suitable for separations based on size or adsorption (depending on polymer identity). Recess geometry (e.g., ribbed, hour-glass or conical) can be optimized to support the structure. Functionality can be either intrinsic or added to such a membrane to perform adsorption separations without the use of particles. For example, cellulose acetate can be treated with base to form cellulose, followed by an oxidant to render it reactive.

In an in situ formation process (either with filled or unfilled structures), the preferred method of formation involves precipitation by means of solvent exchange, such as by introducing the casting solution into the apertures of the inserts by any suitable means, as discussed above. The insert is held to the substrate by mechanical means or by adhesion (e.g., taping). Once the desired volume in the recesses is filled with casting solution, the casting solution in the recesses is contacted with a liquid in which the polymer is insoluble, preferably water, so that the polymer precipitates in the recesses. More specifically, in one embodiment the inserts are placed on a flat substrate, such as a steel or glass plate, thereby forming a floor or bottom to each recess in the insert. The casting solution is then applied to the insert and the recesses therein filled. Once excess casting solution is removed from the insert, the insert (and substrate) is immersed in the liquid in which the polymer precipitates. Through the exchange of water for the solvent, the structure precipitates. The substrate is then removed from the insert. Those skilled in the art will appreciate that the solvent used to prepare the casting solution and the non-solvent can contain a variety of additives.

Alternatively, the holes of the inserts can be filled without the use of a substrate, if the casting solution has a suitably high viscosity. The minimal viscosity necessary depends on the diameter and length of the hole. Thus, smaller holes can hold casting solution of less viscosity than larger holes. For example, holes about 0.040 inches in diameter can hold solutions having a viscosity of at least about 500 cps, while holes having a 0.40 inch diameter require solutions with a viscosity of at least about 50,000 cps to prevent flow out of the hole. One skilled in the art will be able to determine suitable viscosities based upon the particular dimension of the holes without undue experimentation. One particular example is a casting solution containing 30% (w/w) C18 silica solids (15 μm) in a 9% (w/w) Udel P3500 (polysulfone dissolved in N-methylpyrrolidone) solution which has a viscosity of about 800 cps. This solution is suitable for use in holes of about 0.080 in diameter and about the same in length. The viscosity of this solution can be increased to above about 20,000 cps by increasing the C18 solids content to about 40% (w/w). The relationship between solids content and viscosity will vary with particle type.

At the first contact of the polymer with the precipitant, there is virtually instantaneous precipitation, thereby forming a semi-permeable barrier or "skin". This barrier slows the rate of further precipitation creating a more permeable polymer substructure. once precipitation is complete, the initial semi-permeable barrier can be removed, such as by cutting or by abrading the exposed polymer on the surface of the recess. This process also removes excess polymer from the surface, thus making the card more suitable for subsequent assembly. The semi-permeable barrier can be optionally left in place, especially if slightly recessed (e.g., 0.010 inches recessed) from the top surface of the recess, to carry out size-based separations with unfilled structures, as the barrier acts as a micro- or ultra-filtration membrane.

The cast in-place structure assumes the shape of the recesses 12 and results in a self-retaining homogeneous structure akin to a chromatographic column, providing a large surface area (e.g., when particles are included in the polymer matrix) suitable for bind/elute chromatography or for other analytical or biochemical techniques. Suitable driving forces include centrifugation, gravity, capillary action, pressure or vacuum.

Figure 2:
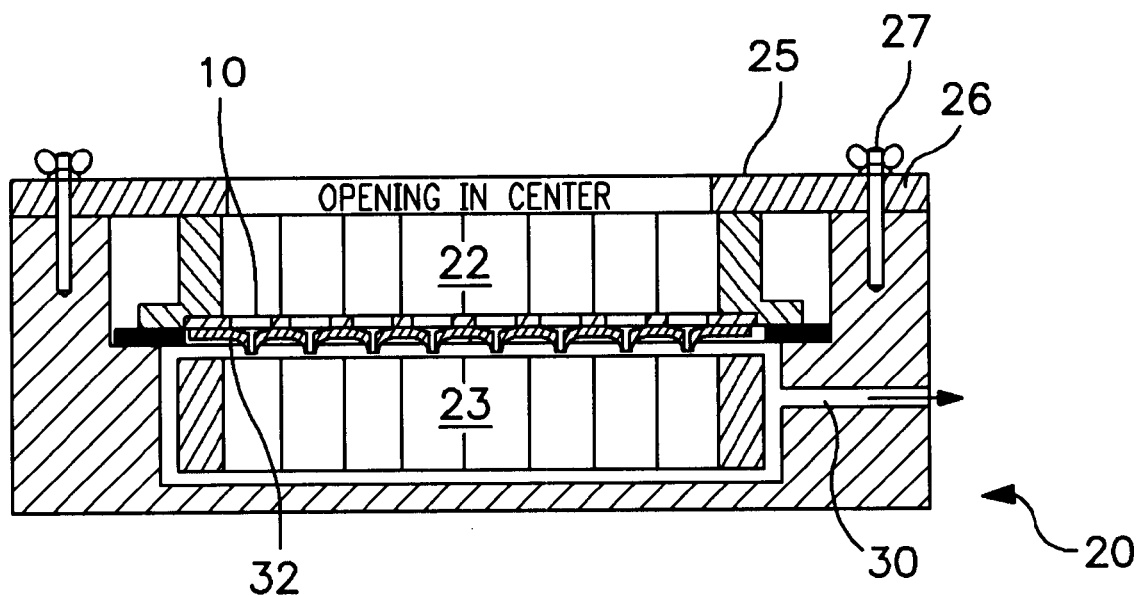
FIG. 2 is a cross-sectional view of a sample preparation device including the insert in accordance with one embodiment of the present invention.

FIG. 2 illustrates one suitable device 20 that forms the sample preparation device of the present invention. The device 20 includes a sample reservoir 22 and a collection reservoir 23 in fluid communication with the sample reservoir 22 through the preferably planar insert or card 10. The insert or card 10 could be applied directly, or can be sealed to a housing 20 by any suitable means, such as mechanically with seal 26, by gluing, welding, such as ultrasonic welding, impulse welding or thermal welding, ensuring that all sample passes through the insert or card (via the filled recesses 12) into the collection reservoir during operation. A mechanical lock down plate 25 coupled to a pair of tie rods actuated by cam lever can be used to secure the device 20 together during operation, but other mechanical means are possible and within the scope of the present invention, such as suitable lock down hardware 27 as shown. The device 20 can be in communication with a source of vacuum via port 30 to provide the driving force for the filtration. A rigid underdrain 32 is provided for support and direction of flow. After filtration, the insert or card 10 can be removed from the device 20 and discarded or used for subsequent analysis or processing. A different insert or card 10 can then be positioned in the device 20, sealed, and is then ready for use.

Figure 3A:
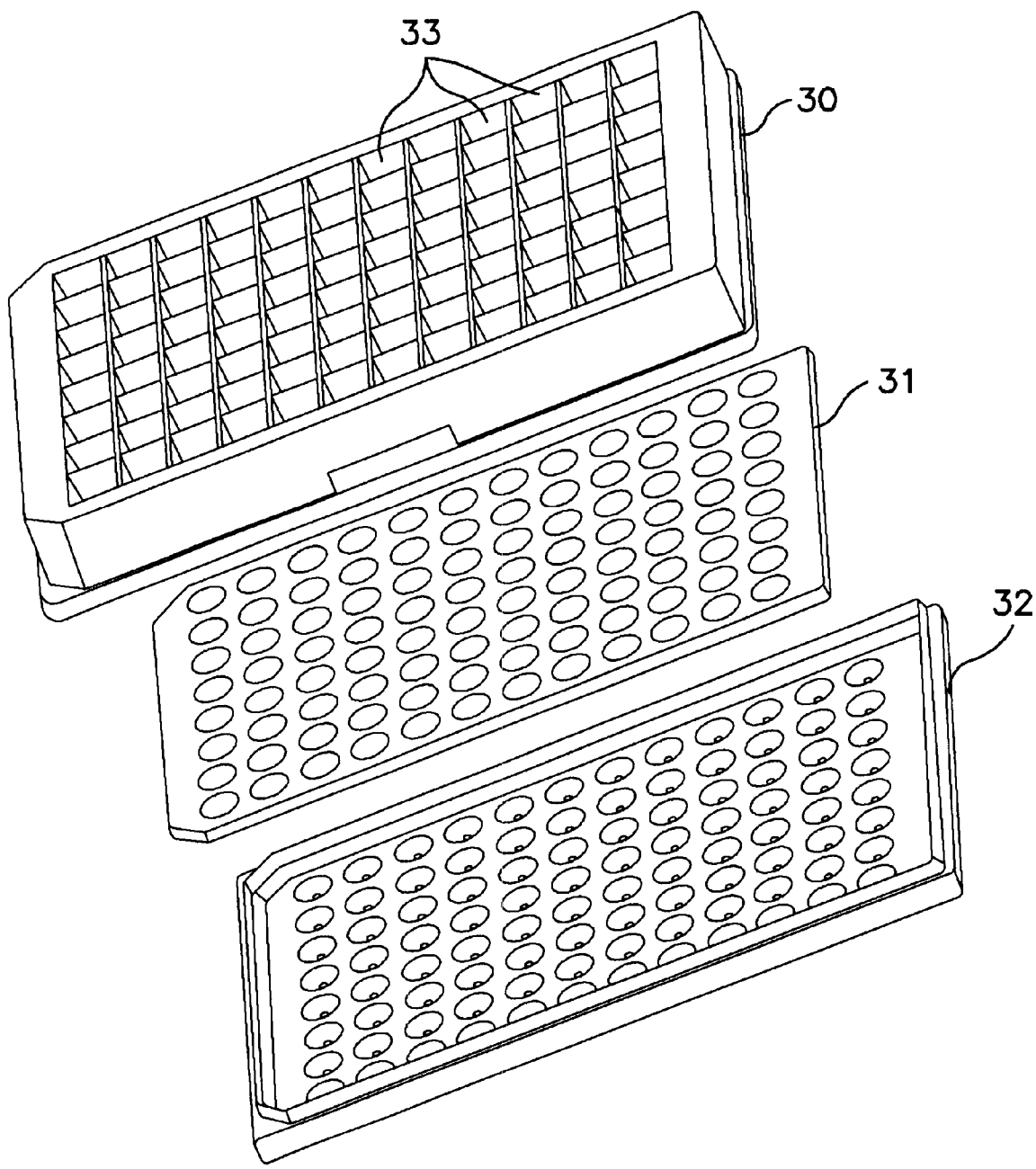
FIG. 3A is a perspective exploded view of one embodiment of the sample preparation device of the present invention.
Figure 3B:
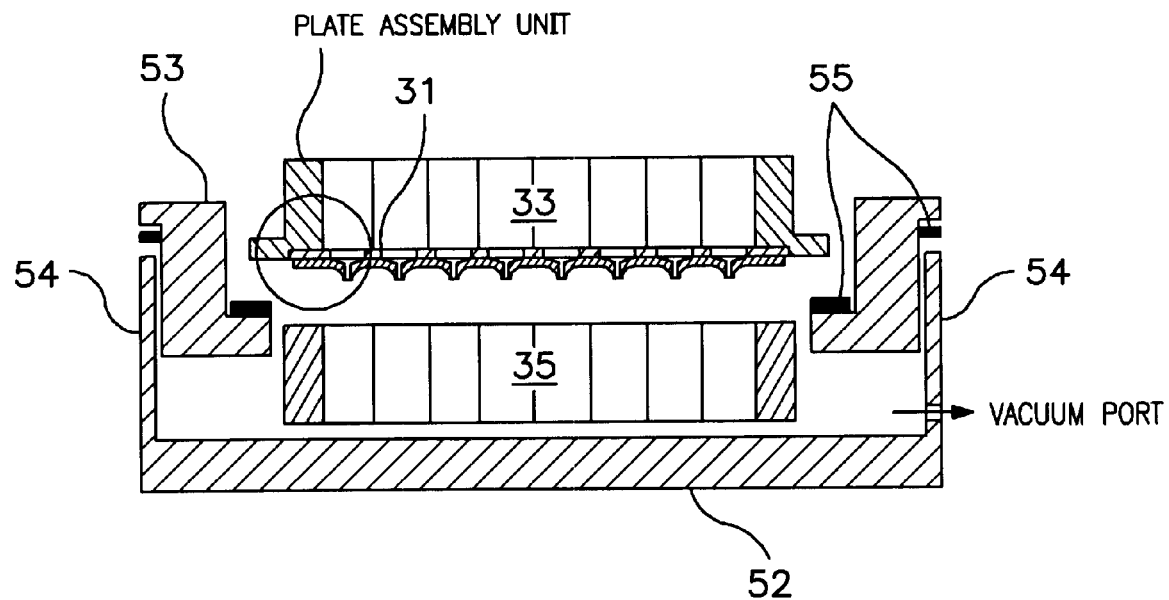
FIG. 3B is a cross-sectional schematic view of a vacuum housing for the sample preparation device of FIG. 3A.
Figure 3C:
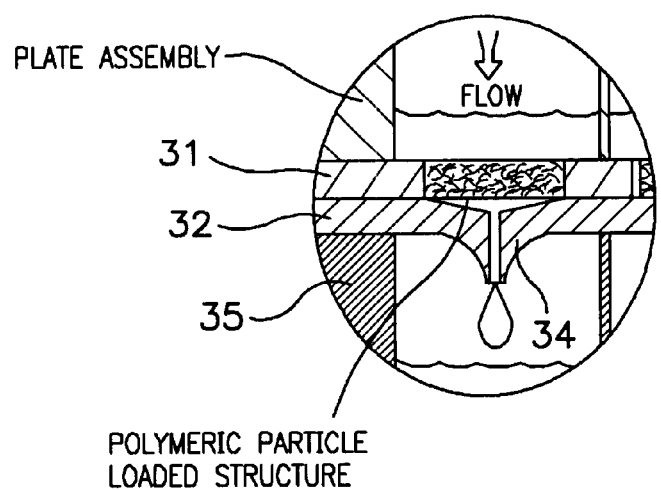
FIG. 3C is an exploded view of a spout of the underdrain of FIG. 3B.

FIG. 3A illustrates a design that can be bonded together as a single unit that can fit into a conventional vacuum housing (FIG. 3B) used for 96 or 384 well filter plates. The upper sample chamber array 30, which contains a plurality of wells 33 (which for a 96× device, can be spaced by 0.36 inch centers; for a 384× device, can be spaced by 0.178 inch centers, etc.) is bonded to the insert 31 along an underdrain assembly 32. As seen in FIGS. 3B and 3C, the underdrain 32 is an array of spouts 34 (preferably in a single part) that is bonded to the underside of the insert 31 and serves to direct the filtrate liquid into a collection vessel or collection reservoir 23. The spouts 34 are sized according to the size of the wells in the insert. When bonded together by suitable means (e.g., glue, such as cyanomethacrylate, UV curable glue, epoxy, silicone, etc., thermal or ultrasonic welding, etc.), the three pieces now form a disposable housing that when placed in a suitable vacuum manifold (with a collection plate 35) will operate as a multiwell (96, 384, 1536×, etc.) sample preparation device (FIG. 3B). The upper chamber and lower spout assemblies can be comprised of a variety of plastics, including polypropylene, polycarbonate, polystyrene, etc.

More specifically, the vacuum chamber for operating the plate assembly unit of FIG. 3A is shown in FIG. 3B. A lower chamber 52 is provided which houses the collection plate 35 as shown. A removable lid 53 is configured to mate with the side walls 54 of the lower chamber 52, and includes elastomeric seals 55 to seal against the side walls and against which the plate assembly unit seals. Once the plate assembly unit is sealed in the device, vacuum or other driving force can be applied to effectuate flow.

The device of FIG. 3A may be assembled by turning the upper housing 30 upside down and precisely dispensing an adhesive onto the partition using a computer controlled liquid delivery device. Onto this, the insert 31 is laid, while taking care to maintain the proper orientation. Once the adhesive in this sub-assembly cures, additional adhesive is applied to the partitions on the side of the insert opposite that adhered to the upper housing 30. The underdrain 32 is set upon this additional adhesive and carefully oriented for axial alignment of recesses. The result after curing is a disposable, high throughput, sample preparation device ready to fit into current state-of-the-art robotics.

Where the application dictates media having different chemistries, the device 20 can be adapted to accommodate more than a single insert at any given time. For example, two or more inserts can be aligned so that their respective recesses are in fluid communication with one another. Alternatively or in addition, one or more holes in a single insert can be filled with media having different chemistries.

As can be seen from the foregoing, the insert or card 10 can be used by itself or can be bonded or coupled to other elements to provide a wider range of function. Solutes that have been treated by the card 10 can be collected and transferred to analytical equipment for further analysis. Alternatively, once solute is bound to the card 10, the card itself can be inserted into an analytical instrument such as a MALDI TOF mass spectrometer, and analyzed directly by laser interrogation, for example, thereby eliminating a transfer step. More specifically, a desorbing matrix can be applied to the sample bound to the structure in the insert, such as a matrix including acetonitrile, which desorbs the sample for MALDI TOF mass spectrometry, and also helps mediate the effect of the laser so that the sample is not destroyed.

Without limitation, the following example illustrates the objects and advantages of the present invention.

EXAMPLE 1

C18, 15 um Silica Particle Loaded Membrane Cast in Place

In a small vessel, 10 grams of a 9% (w/w) polysulfone solution (Amoco, P3500) was prepared in N-methyl-2- pyrrolidone. To this, 2 grams of C18, 200 Å, 15 μm silica (Millipore, PN 85864) was added and mixed thoroughly with a spatula. The mixture was allowed to equilibrate for 2 hours at room temperature, then mixed again. Using a pipette or eye dropper, 25–50 μl of casting solution was dispensed into a suitable fixture, such as the recesses of a 3"×5"×0.06" polypropylene insert pre-drilled with 384 0.1 inch diameter holes at 0.178 inch center spacing which has been taped to a glass plate (substrate). Once added, a bar was drawn over the card surface to ensure that the solution filled the recesses. Care was taken to ensure that bubbles did not form. The device was immersed in water for ca. 0.5 hours. After this period, the unit was removed and a razor blade was used to remove excess polymer. The card was then removed from the glass plate and was re-immersed in the water for an additional 0.5 hours to complete solvent exchange. The insert was then removed from the water and allowed to air dry.

EXAMPLE 2

A polymer solution (about 25 ml) of polysulfone is prepared in N-methylpyrrolidone to about 9% w/w in polymer solids in an about 100 ml beaker. To this solution, particles are added (which may or may not have adsorptive properties) while constantly mixing until the lacquer is of the consistency of plaster (approximately 40% solids and 25,000 cps). Using a flexible spatula, the lacquer is spread into the holes of a predrilled card (same as Example 1) which is being held by the outer edges. Once the holes are filled, the excess on the exterior of both sides is removed such as by scraping, and the card is immersed in a water bath at 80 C. After the structure is precipitated and desolvenated (about 1 hour), the card is removed and the excess polymer above the plane of the card surface is removed such as with a razor blade or wiping with a cloth. The card is then re-immersed and agitated in a water bath for about 5 minutes to remove particulate matter, and is then removed and allowed to dry.

EXAMPLE 3

The device of FIG. 3 is placed into the top (spouts facing down) of a common vacuum housing 40 as shown in FIG. 4. It is sealed to a removable lid 42 such as by elastomeric seals 43. A collection tray 35 is underneath within the lower chamber 45. A conditioning solution is added to the upper sample chambers and the vacuum turned on to pull the solution through. Sample is then applied. As the vacuum pulls the sample solution through, the components of interest adsorb to the polymeric structure within the insert, while the contaminants flow into the collection vessel 35. A wash solution is then added to the upper chamber 30 (with the vacuum on) to rinse away trace contaminants. The vacuum is turned off and the collection vessel 35 is replaced with a clean one. The unit is re-assembled and a suitable desorption solution is added to the upper sample chambers. As this solution flows through the insert, it desorbs the components of interest, which are captured by the clean collection vessel 35.

EXAMPLE 4

Desalting of Peptides

A 0.02" cylindrical hole was bored into the center of a 1.75×1.75×0.04" piece of flat polypropylene plastic using a sharp point. Into this hole, a slight excess of lacquer was added consisting of 9% (w/w) polysulfone (UDEL P3500): 91% (w/w) N-methylpyrrolidone containing 30% (w/w) of C18-200 Å-15 μm spherical silica particles using the tip of a spatula. The plastic was then immersed into an ambient temperature water bath for 1 hour to precipitate the polymer. After this period, the plastic substrate was removed and polymer precipitated on the exterior surfaces was cut off with a sharp razor blade. The cast-in-place structure was then placed on top of a vacuum flask and washed liberally with water (under vacuum) to ensure that the "cast in place" polymer structure was completely solvent exchanged.

Figure 4A:
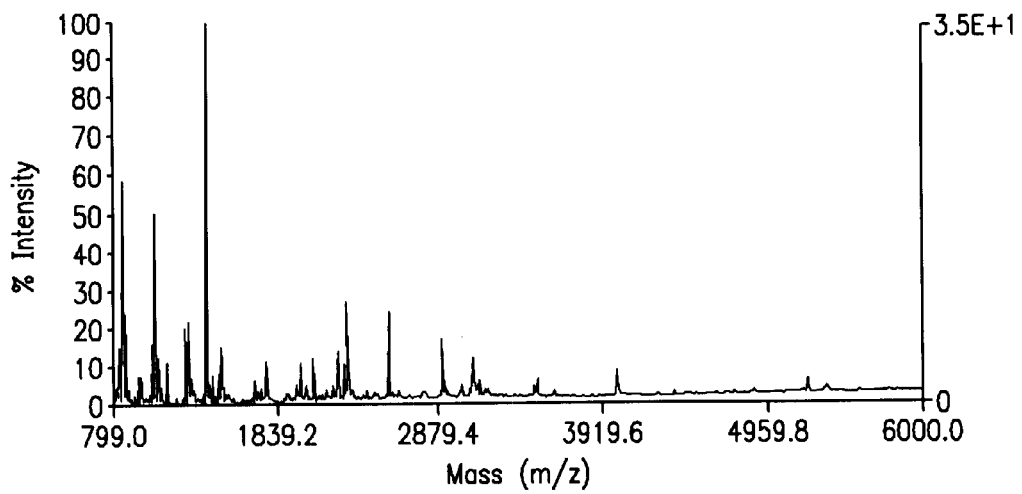
FIGS. 4A and 4B are graphs of the mass spectrum of desalted peptides in accordance with Example 4.
Figure 4B:
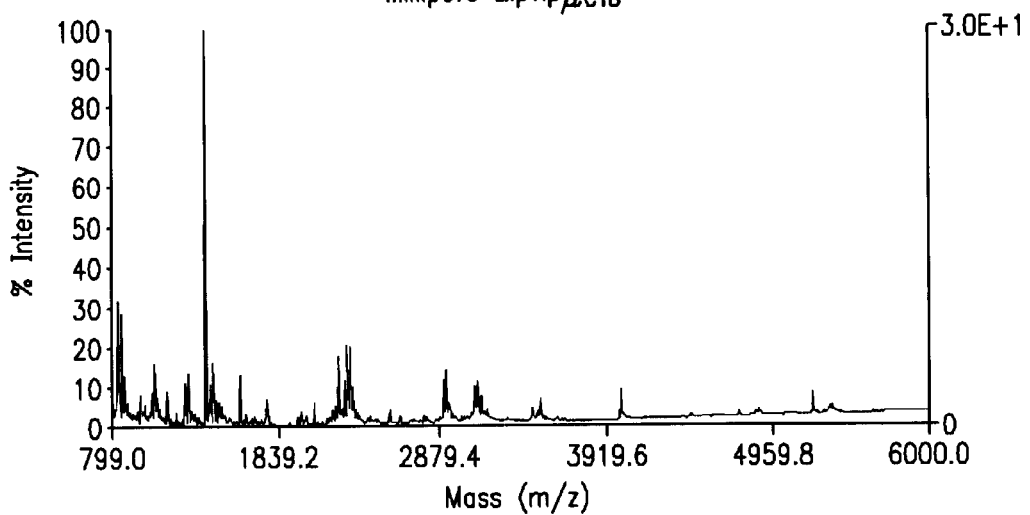

Following washing, the structure was contacted tightly on one side with an absorbent paper towel. Two microliters of methanol was deposited directly onto the other side of the structure and allowed to pass into the plug by capillary action. This step was followed by the addition of 5 μl of 0.1% (v/v) trifluoroacetic acid (TFA), which entered the plug in the same way. Onto the equilibrated structure, 1 μl of 1 M guanidine hydrochloride (GuHCl) containing 2.5 picomoles of beta casein tryptic peptides was added and allowed to absorb into the plug by capillary action for about 1 min. Any remaining sample on top of the plug was passed through using positive pressure. The structure was then washed with 10 μl of water containing 0.1% (v/v) TFA to remove GuHCl. This was performed by overlaying the structure with the liquid followed by forcing it through with positive pressure using a 1 cc syringe containing a gasket that formed a seal around recess. Then, 3 μl of 60% acetonitrile/40% distilled water containing 0.1% TFA was carefully deposited onto the structure. The solution was driven through the structure again using positive pressure, thus forming a drop on the underside. Using a pipette, the drop (containing eluted peptides) was then collected, spotted onto a MALDI-TOF MS target, overlaid with matrix (α-cyano-4 hydroxycinnamic acid) and analyzed. (FIG. 4A). Results of a control experiment using Millipore ZipTip$_{\mu C18}$® micro-solid phase extraction pipette tips for peptide desalting are shown in FIG. 4B.

EXAMPLE 5

Desalting of Peptides with Direct MALDI-TOF MS Analysis

Figure 5A:
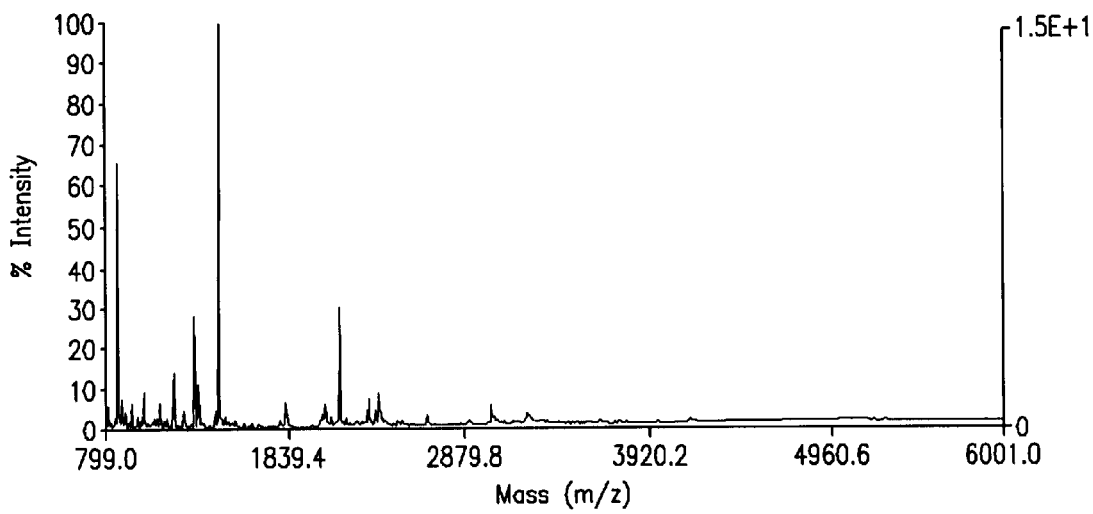
FIGS. 5A and 5B are graphs of the mass spectrum of desalted peptides in accordance with Example 5.
Figure 5B:
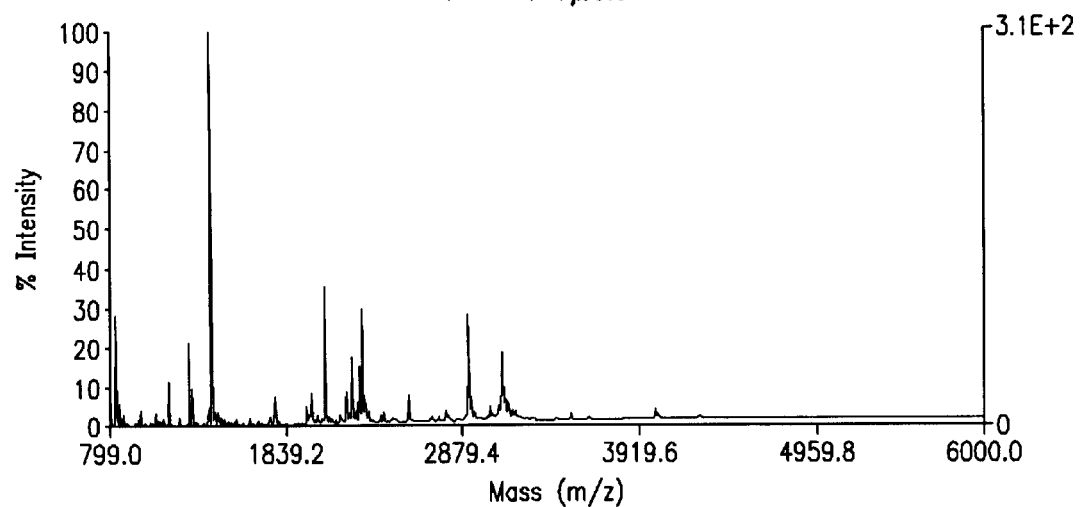

Using the device described in Example 4, 2 μl of methanol was deposited directly onto the free side of the structure and allowed to pass into the plug by capillary action. This step was followed by the addition of 5 μl of 0.1% (v/v) TFA, which entered the plug in the same way. Onto the equilibrated structure, 1 μl of 1 M guanidine hydrochloride (GuHCl) containing 2.5 picomoles of beta casein tryptic peptides was added and allowed to absorb into the plug by capillary action for about 1 min. Any remaining sample on top of plug was passed through using positive pressure. The structure was then washed with water containing 0.1% (v/v) TFA to remove GuHCl using positive pressure (see Example 4). Once the sample is washed and air dried, 0.5 μl of matrix (10 mg/ml α-cyano-4 hydroxycinnamic acid, 60% acetonitrile, 0.3% TFA) was carefully deposited onto the plug and allowed again to air dry. The plastic substrate was then snapped into a PE BioSystems (Framingham, Mass.) MALDI sample plate holder (PIN V700314) in the same orientation. The plate holder was inserted into a PE BioSystems Voyager™ MALDI-TOF MS mass spectrometer with delayed extraction and the matrix spot was analyzed directly (FIG. 5A). In a control experiment, peptides were desalted using a ZipTip$_{\mu C18}$® and eluted from tip using 0.5 μl of matrix directly onto MALDI-TOF MS sample plate (FIG. 5B).

EXAMPLE 6

Desalting of Oligonucleotides

Figure 6A:
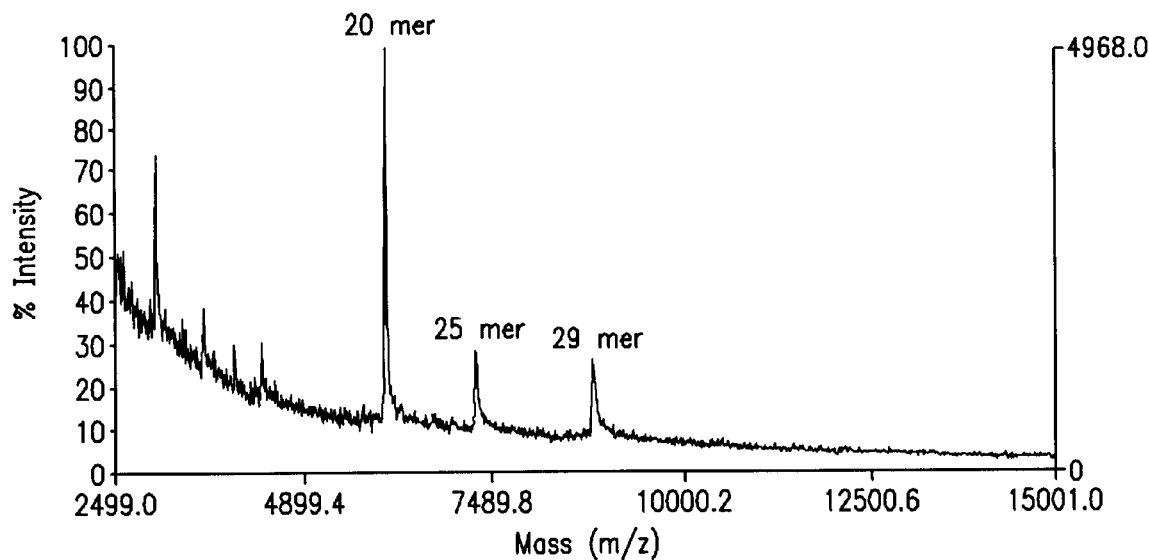
FIGS. 6A and 6B are graphs of the mass spectrum of desalted oligonucleotides in accordance with Example 6.
Figure 6B:
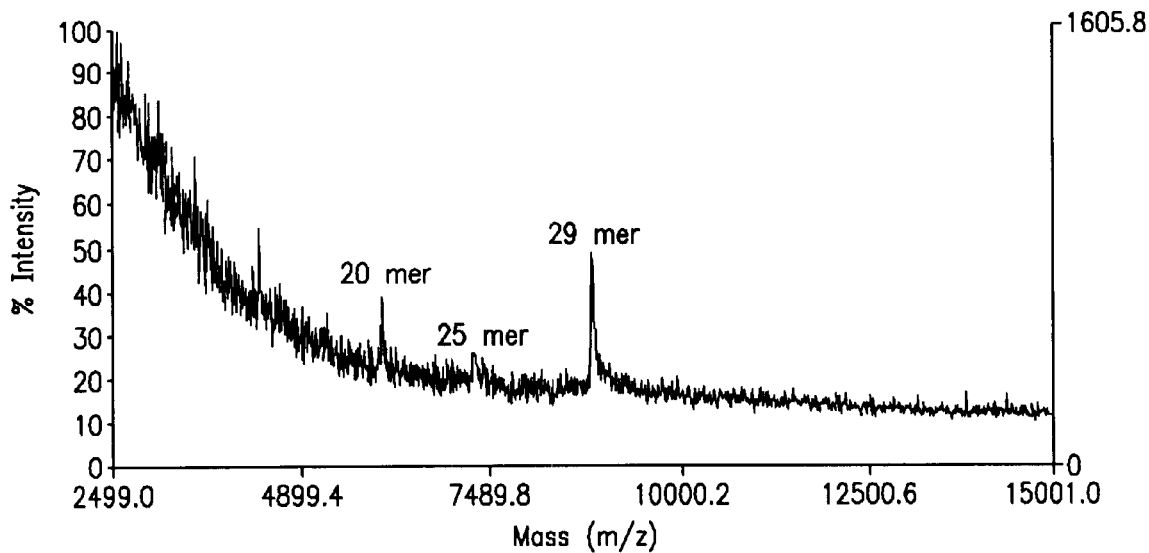

Using the device described in Example 4, 2 µl of methanol were deposited directly onto the free side of the structure and allowed to pass into the plug by capillary action. This step was followed by the addition of 5 µl of 50 mM triethylamine acetate buffer, pH 7.0, which entered the plug in the same way. Onto the equilibrated structure, 3 µl of 50 mM triethylamine acetate buffer, pH 7.0, containing 5 pmole each of three oligonucleotides (20, 25 and 29 mer) and 165 mM NaCl was added and allowed to absorb into the plug by capillary action for about 1 min. Any remaining sample on top of the plug was passed through using positive pressure. The structure was washed with 10 µl of water using positive pressure (see example 1) and allowed to air dry. Then, 2 µl of 50% acetonitrile/50% distilled water was carefully deposited onto the structure. To elute, a sufficient positive pressure was applied to drive the solution through the structure thus forming a drop on the underside. Using a pipette, the drop containing the desorbed oligonucleotides was collected, spotted onto a MALDI-TOF MS target, overlaid with HPA matrix (hydroxypiccolinic acid) and analyzed (FIG. 6A). In a control experiment, oligonucleotides were desalted using a ZipTip$_{\mu C18}$® and eluted from tip using 2 µl of 50% acetonitrile/50% distilled water directly onto MALDI-TOF sample plate (FIG. 6B) then overlaid with matrix.

EXAMPLE 7

Desalting of Oligonucleotides with Direct MALDI-TOF MS Analysis

Figure 7:
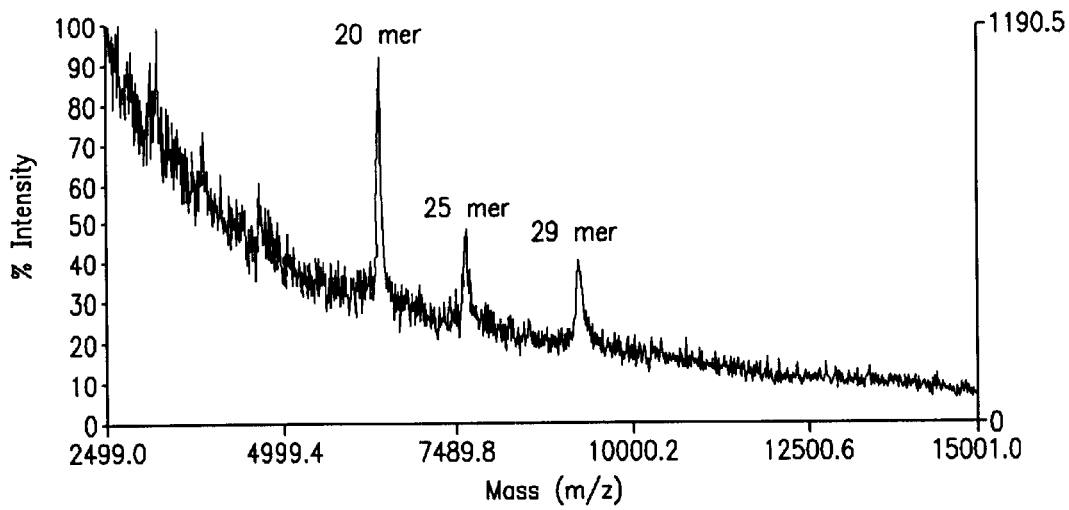
FIG. 7 is a graph of the mass spectrum of desalted oligonucleotides in accordance with Example 7.

Using the device described in Example 4, 2 µl of methanol were deposited directly onto the free side of the structure and allowed to pass into the plug by capillary action. This step was followed by the addition of 5 µl of 50 mM triethylamine acetate buffer, pH 7.0, which entered the plug in the same way. Onto the equilibrated structure, 3 µl of 50 mM triethylamine acetate buffer, pH 7.0, containing 5 pmole each of three oligonucleotides (20, 25 and 29 mer) was added and allowed to absorb into the plug by capillary action for about 1 min. Any remaining sample on top of the plug was forced through using positive pressure. The structure was liberally washed with water using positive pressure (see Example 4). Once washed and air dried, 1.0 µl of matrix (45 mg/ml hydroxypiccolinic acid, 5 mg/ml ammonium citrate, 45% acetonitrile) was carefully deposited onto the structure and again allowed to air dry. The plastic substrate was then snapped into a PE BioSystems (Framingham, Mass.) disposable MALDI sample plate holder (P/N V700314) in the same orientation. The carriage was inserted in a PE BioSystems Voyager™ MALDI-TOF MS mass spectrometer with delayed extraction and the matrix spot was analyzed directly. (FIG. 7).

EXAMPLE 8

Affinity Capture of Peptides and Proteins

A 0.02" cylindrical hole was bored into the center of a 1.75×1.75×0.04" piece of polypropylene plastic using a sharp point. Into this hole, a slight excess of lacquer was added consisting of 10% (w/w) polystyrene (Dow Chemical, Styron 685D): 90% (w/w) N-methylpyrrolidone containing 30% (w/w) of imidodiacetic acid coated-200 Å-15 µm spherical silica particles using the tip of a spatula. The plastic was then immersed into an ambient temperature water bath for 1 hour to precipitate the polymer. After this period, the plastic substrate was removed and polymer precipitated on the exterior surface was cut off with a sharp razor blade. The cast-in-place structure was then placed on top of a vacuum flask and washed liberally with water (under vacuum) to ensure that the polymer structure was solvent exchanged. Following washing, the structure was contacted tightly on one side with an absorbent paper towel. To charge the metal chelate resin with copper ions, 2 µl of methanol were deposited directly onto the free side of the structure and allowed to pass into the plug by capillary action onto an absorbent paper towel, followed by 5 µl of 50% acetonitrile, 5 µl of 200 mM cupric sulfate solution, then 5 µl of 0.1% acetic acid containing 10% acetonitrile, respectively, which entered the plug in the same way.

Part 1: Enrichment of Phosphopeptides from a Peptide Digest

Figure 8A:
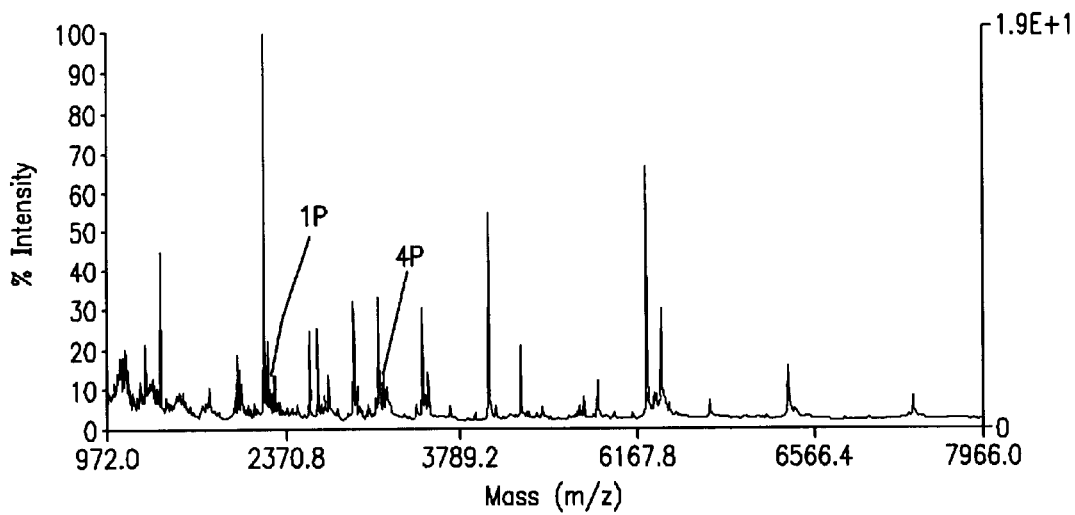
FIG. 8A is a graph of the mass spectrum of peptides in accordance with Example 8.
Figure 8B:
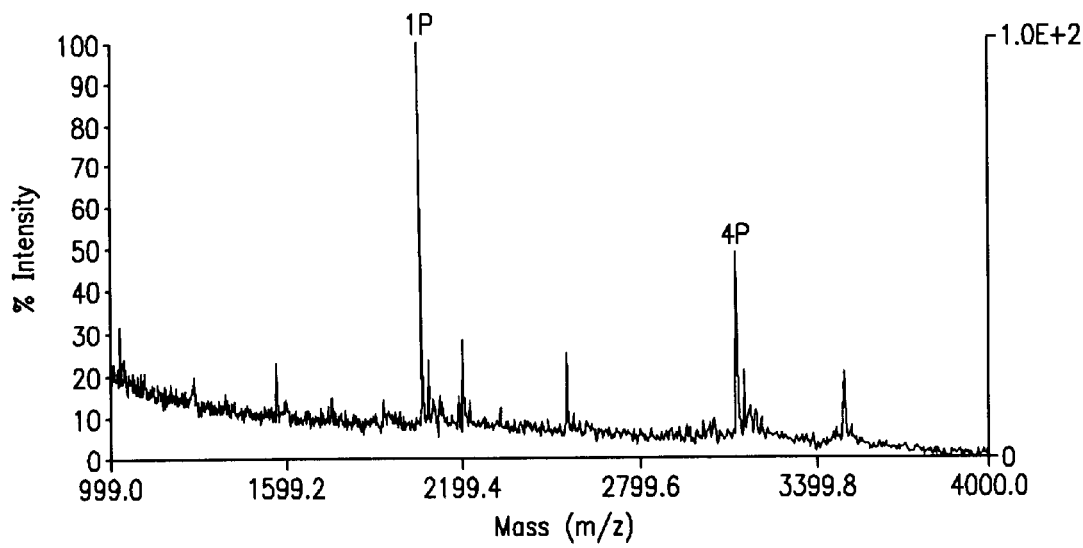
FIGS. 8B and 8C are graphs of the mass spectrum of phosphopeptides in accordance with Example 8.
Figure 8C:
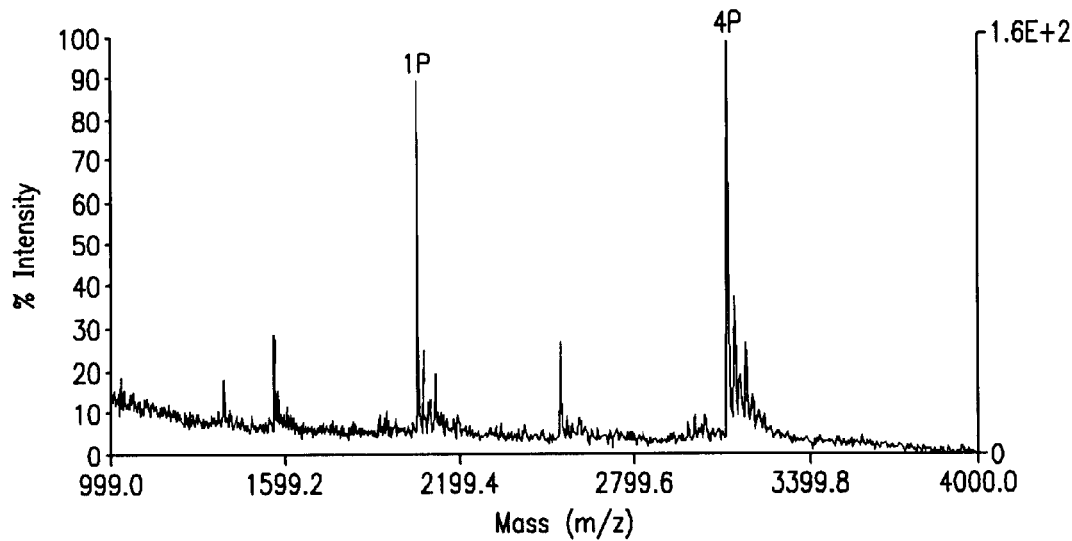

After charging the structure with copper ions, 5 µl of 50 mM 2-(N-morpholino)-ethanesulfonic acid, pH 5.5 (MES buffer) containing 10% acetonitrile was deposited directly onto the free side of the plug and allowed to absorb by capillary action. Onto the equilibrated structure, 2 µl of MES buffer, pH 5.5 containing 10% acetonitrile and 2.5 picomoles of beta casein tryptic peptides was added and allowed to absorb into the plug by capillary action for about 1 min. Any remaining sample on top of the plug was forced through using positive pressure. The plugs were washed liberally with 0.1% acetic acid to remove contaminants using positive pressure (see Example 4). Once washed, 2 µl of 2% ammonium hydroxide was carefully deposited onto the plug surface. The solution was driven through the structure using a slight positive pressure thus forming a drop on the underside. The drop containing eluted peptides (1P and 4 P phosphopeptides) was then collected, spotted onto a MALDI-TOF MS target, overlaid with THAP matrix (10 mg/ml 2,4,6trihydroxyacetophenone, 60% acetonitrile, 2% TFA, 10 mM ammonium citrate) and analyzed (FIG. 8B). In a control experiment, phosphopeptides were enriched using a Millipore ZipTip$_{MC}$® pipette tip charged with copper ions. The peptides (1P and 4P) were eluted from tip using 2 µl of 5% ammonium hydroxide directly onto MALDI-TOF MS sample plate (FIG. 8C). FIG. 8A depicts spectra of total peptide digest prior to phosphopeptide (1P and 4P) enrichment.

Figure 8D:
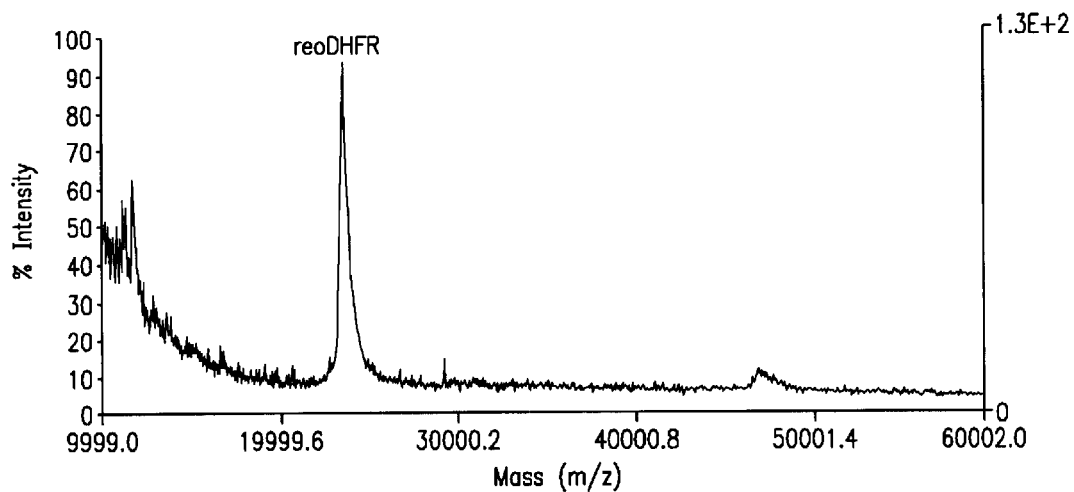
FIGS. 8D and 8E are graphs of the mass spectrum of recombinant his-tagged protein in accordance with Example 8.
Figure 8E:
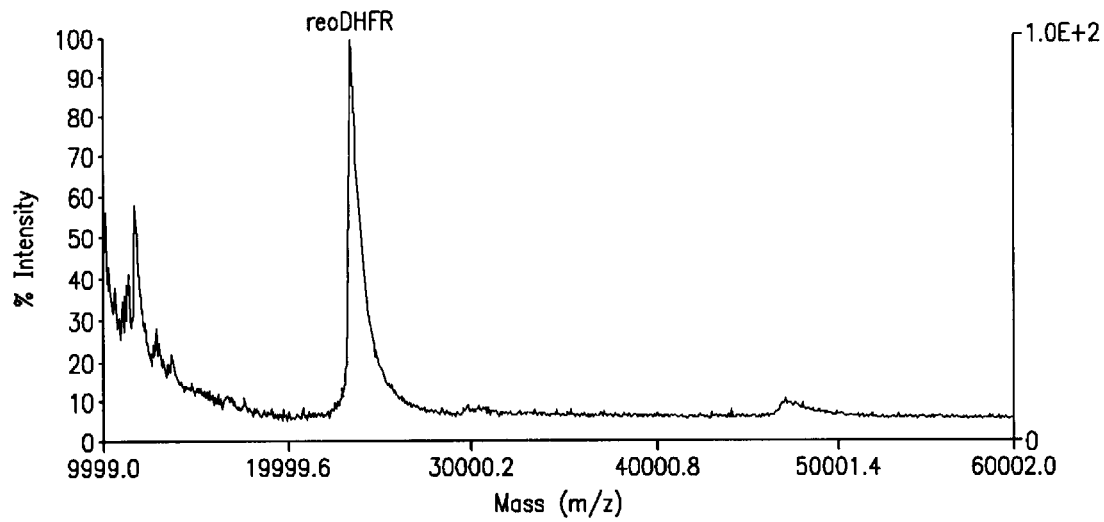

Part 2: Enrichment of 6×His Tagged Recombinant Protein (rec DHPR) from a E. coli Cell Supernatant After charging the structure with copper ions (see above), 5 µl of 8 M Urea, 0.1 M NaH$_2$PO$_4$, 0.01 M Tris-HCL, pH 8.0, was deposited directly onto the free side of the structure and forced into the plug by positive pressure. Subsequently, 1 µl of E. coli cell lysate supernatant in 8 M Urea, 0.1 M NaH$_2$PO$_4$, 0.01 M Tris-HCL, pH 8.0 was added and allowed to absorb into the plug by capillary action for about 1 min. Any remaining sample on top of the plug was passed through using positive pressure. The structure was then washed liberally with 10 mM ammonium bicarbonate buffer containing 20% acetonitrile (pH≈8.0) and 5 mM MES, pH 6.5 buffer, respectively, to remove contaminants. Once washed, 3 µl of 5% acetic acid was carefully deposited onto the structure. A slight positive pressure was applied sufficient to drive the solution through the structure forming a drop on the underside. The drop containing recombinant protein (recDHFR) was then collected, spotted onto a MALDI-TOF MS target, overlaid with matrix (10 mg/ml sinnapinic acid, 60% acetonitrile, 0.3% TFA) and analyzed (FIG. 8D). In a control experiment, protein was enriched using a ZipTip$_{MC}$® charged with copper ions. The protein was eluted from the tip using 3 μl of 5% acetic acid directly onto MALDI-TOF MS sample plate and overlaid with matrix (FIG. 8E).

EXAMPLE 9

Affinity Capture of Peptides and Proteins with Direct MALDI-TOF MS Analysis

Part 1: Enrichment of Phosphopeptides from a Peptide Digest

Figure 9A:
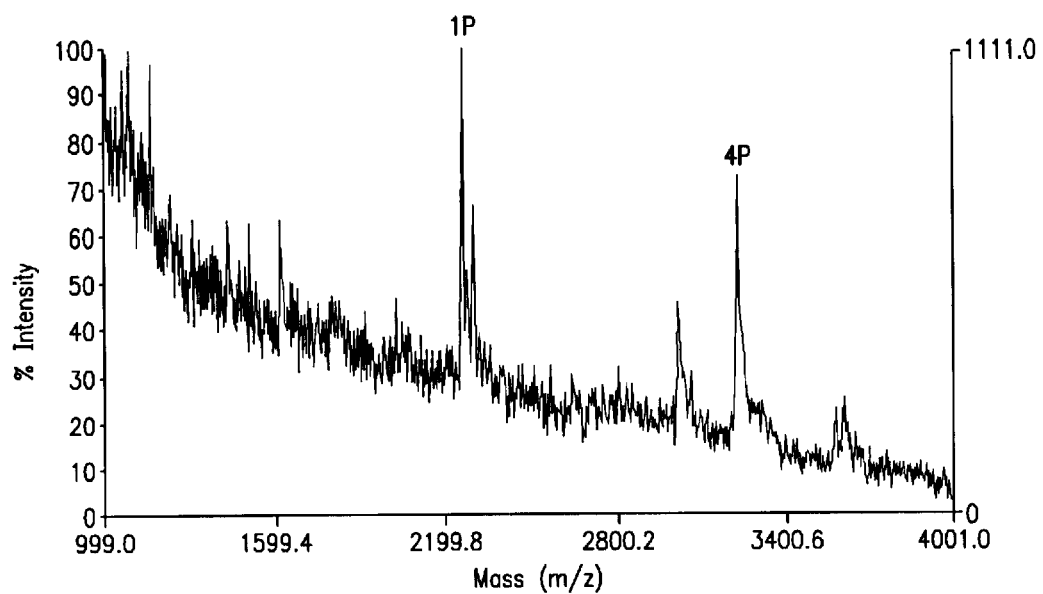
FIG. 9A is a graph of the mass spectrum of phosphopeptides in accordance with Example 9.

Using the device described in Example 8 charged with copper ions, 2 μl of methanol were deposited directly onto the free side of the structure and allowed to pass into the plug by capillary action. After this step, 5 μl of 50 mM 2-(N-morpholino)-ethanesulfonic acid, pH 5.5 (MES buffer) containing 10% acetonitrile was deposited directly onto the free side of the structure and allowed to pass into the plug by capillary action. Onto the equilibrated structure, 2 μl of MES buffer, pH 5.5 containing 10% acetonitrile and 2.5 picomoles of beta casein tryptic peptides was added and allowed to absorb into the plug by capillary action for about 1 min. Any remaining sample on top of the plug was forced through using positive pressure. The structure was then washed with 0.1% acetic acid to remove contaminants (see Example 4). Once washed, 1.0 μl of THAP matrix (10 mg/ml 2,4,6-trihydroxyphenone, 60% acetonitrile/40%, 2% TFA), was carefully deposited onto the structure and allowed to air dry. The plastic substrate was then snapped into a PE BioSystems (Framingham, Mass.) disposable MALDI sample plate holder (P/N V700314) in the same orientation The carriage was inserted in a PE BioSystems Voyager™ MALDI-TOF MS mass spectrometer with delayed extraction and the matrix spot was analyzed directly (FIG. 9A).

Figure 9B:
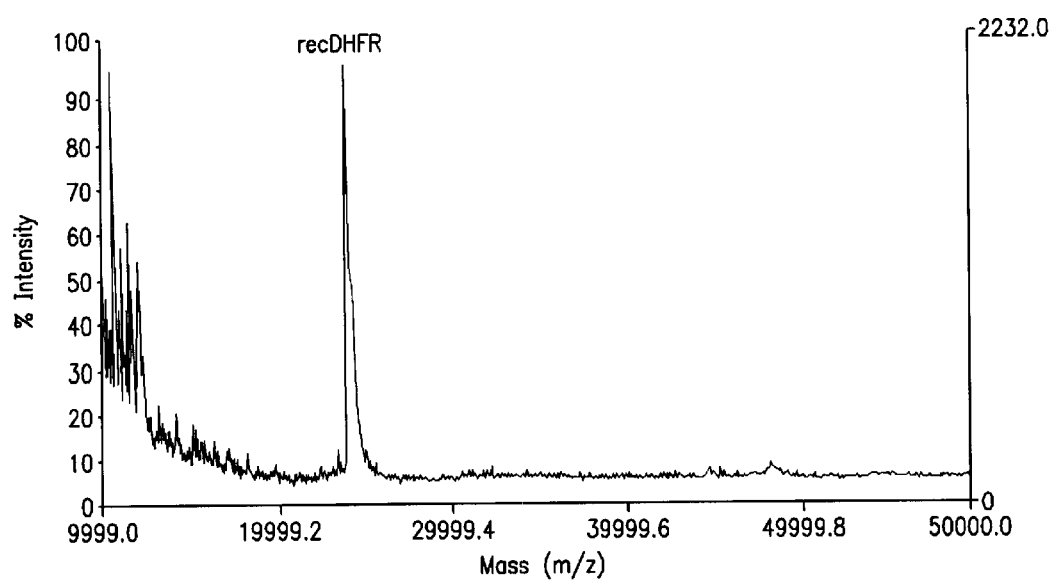
FIG. 9B is a graph of the mass spectrum of recombinant his-tagged protein in accordance with Example 9.

Part 2: Enrichment of 6×His Tagged Recombinant Protein (rec DHFR) from a *E. coli* Cell Supernatant Using the device described in Example 8 charged with copper ions, 2 μl of methanol were deposited directly onto the free side of the structure and allowed to pass into the plug by capillary action. Then, 5 μl of 8 M Urea, 0.1 M $NaH_2PO_4$, 0.01 M Tris-HCL, pH 8.0 was deposited directly onto the free side of the structure and allowed to pass into the plug by positive displacement. Onto the equilibrated structure, 1 μl of *E. coli* cell lysate supernatant in 8 M Urea, 0.1 M $NaH_2PO_4$, 0.01 M Tris-H CL, pH 8.0 was added and allowed to absorb into the plug by capillary action for about 1 min. Any remaining sample on top of the plug was forced through using positive pressure. The structure was then liberally washed using positive pressure with 10 mM ammonium bicarbonate buffer containing 20% acetonitrile (pH≈8.0) and 5 mM MES, pH 6.5 buffer, respectively, to remove contaminants. Once washed, 1.0 μl of matrix (10 mg/ml sinnapinic acid, 60% acetonitrile, 0.3% TFA) was carefully deposited onto the structure and allowed to air dry. The plastic substrate was then snapped into a PE BioSystems (Framingham, Mass.) disposable MALDI sample plate holder (P/N V700314) in the same orientation. The plate holder was inserted in a PE BioSystems Voyager™ MALDI-TOF MS mass spectrometer with delayed extraction and the matrix spot was analyzed directly (FIG. 9B).

What is claimed is:

1. A housing having a thickness, said housing have a first surface and a second surface spaced from said first surface by said housing thickness, said housing having one or more apertures formed through said housing, each of said one or more apertures defined by solid walls extending through said thickness of said housing and containing a self-retaining structure, chemically self-adhered to said solid walls, comprising a porous matrix, said structure being coterminous with said first surface and said second surface, said structure having an aspect ratio of less than about 20.

2. The housing of claim 1, wherein said porous matrix comprises a plurality of sorptive particles entrapped therein.

3. The housing of claim 1, wherein said porous matrix is polymeric.

4. The housing of claim 1, wherein said structure is functionalized for adsorption.

5. The housing of claim 1, wherein said housing is a planar substrate.

6. The housing of claim 1, wherein said housing is a multi-well plate.

7. A housing having a thickness, a length and a width, said housing having a first surface and a second surface spaced from said first surface by said thickness, the dimensions of said thickness being less than the dimensions of said length and/or said width, said housing having one or more apertures formed through said housing and defined by solid walls extending through said thickness, each of said one or more apertures containing a self-retaining structure, chemically self-adhered to said solid walls and coterminous with said first and second surfaces, comprising a porous matrix.

8. The housing of claim 7, wherein said porous matrix comprises a plurality of sorptive particles entrapped therein.

9. The housing of claim 7, wherein said porous matrix is polymeric.

10. The housing of claim 7, wherein said structure is functionalized for adsorption.

11. The housing of claim 7, wherein said housing is a planar substrate.

12. The housing of claim 7, wherein said housing is a multi-well plate.

13. A sample preparation device, comprising a sample reservoir and a collection reservoir spaced from said sample reservoir, and a substrate between said sample reservoir and said collection reservoir, said substrate have a first surface and a second surface spaced from said first surface defining a thickness, said substrate comprising one or more recesses formed therethrough, each of said one or more recesses defined by solid walls extending through said thickness and containing a self-retaining structure, chemically self-adhered to said solid walls, comprising a porous matrix, said structure being coterminous with said first surface and said second surface, said structure having an aspect ratio of less than about 20.

14. The sample preparation device of claim 13, wherein said porous matrix comprises a plurality of sorptive particles.

15. The sample preparation device of claim 13, further comprising an underdrain having one or more spouts, each in fluid communication with a respective said one or more recesses of said substrate.

16. The sample preparation device of claim 15, wherein said one or more spouts direct fluid into said collection reservoir.

17. The sample preparation device of claim 15, wherein said sample reservoir and said underdrain are bonded to said substrate.

18. The sample preparation device of claim 13, wherein said substrate is removable from said housing.

19. A sample preparation device for use with a chamber in communication with a driving force, said device comprising:

a sample reservoir; a substrate fixed to said sample reservoir, said substrate having a first surface and a second surface spaced from said first surface, said substrate comprising at least one recess formed therethrough, said at least one recess defined by solid walls extending through said substrate and containing a self-retaining structure, chemically self-adhered to said solid walls, comprising a porous matrix, said structure being coterminous with said first and second surfaces; and a spout fixed to said at least one recess for directing flow into said chamber.

20. The sample preparation device of claim 19, wherein said substrate comprises a plurality of recesses.

21. A housing having a thickness, said housing have a first surface and a second surface spaced from said first surface by said housing thickness, said housing having one or more apertures formed through said housing, each of said one or more apertures defined by solid walls extending through said thickness and containing a structure, chemically self-adhered to said solid walls, comprising a porous matrix, said structure being coterminous with said first surface and said second surface, said structure being self-retaining in said housing by adhesion.

22. A filtration device comprising a substrate having first and second spaced surfaces defining a housing thickness and an array of spaced, independent apertures formed through said housing thickness, each of said independent apertures defined by solid walls extending through said thickness and containing a formed porous matrix coterminous with said first and second surfaces, the porous matrix in each independent aperture being segregated from the porous matrix in each other different independent aperture, said first and second surfaces in the space between said apertures being devoid of said porous matrix, said porous matrix adapted to be self-retaining in said apertures and being chemically adhered to said solid walls.

* * * * *